United States Patent
Heincke

(10) Patent No.: US 6,297,420 B1
(45) Date of Patent: Oct. 2, 2001

(54) METHOD OF SELECTING AN ITEM TO MATCH A PERSON'S SKIN TONE

(76) Inventor: Arno J. Heincke, 11 Mead Ave., Beacon, NY (US) 12508

( * ) Notice: Subject to any disclaimer, the term of this patent is extended or adjusted under 35 U.S.C. 154(b) by 0 days.

(21) Appl. No.: 09/430,271

(22) Filed: Oct. 29, 1999

(51) Int. Cl.⁷ .................................................. A61F 13/00
(52) U.S. Cl. .................................. 602/41; 602/54; 602/58
(58) Field of Search ........................ 602/41–59; 128/888

(56) References Cited

U.S. PATENT DOCUMENTS

| | | | |
|---|---|---|---|
| 402,371 | 12/1998 | Haynes et al. ...................... D24/189 |
| 2,905,174 | 9/1959 | Smith ................................... 128/156 |
| 3,687,136 | 8/1972 | Carmody .............................. 128/156 |
| 4,161,176 | 7/1979 | Harris, II et al. .................... 128/155 |
| 5,120,325 | 6/1992 | Dow, Jr. ............................... 604/304 |
| 5,586,971 | 12/1996 | Newman ............................... 602/58 |
| 6,177,093 | 1/2001 | Lombardi et al. . |

*Primary Examiner*—Kim M. Lewis
(74) *Attorney, Agent, or Firm*—Milde, Hoffberg & Macklin, LLP

(57) ABSTRACT

A method of selecting or manufacturing a matching skin tone item, such as a bandage; including sterile wrapped adhesive bandages, the methods including matching by scanner, manufacturing by printing, developing skin tone colors.

8 Claims, 3 Drawing Sheets

FIG.1
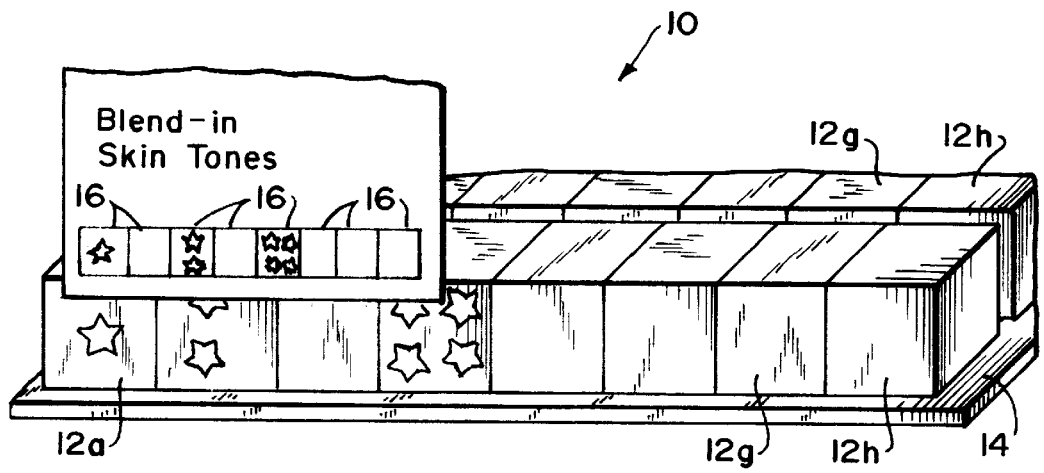
FIG.2
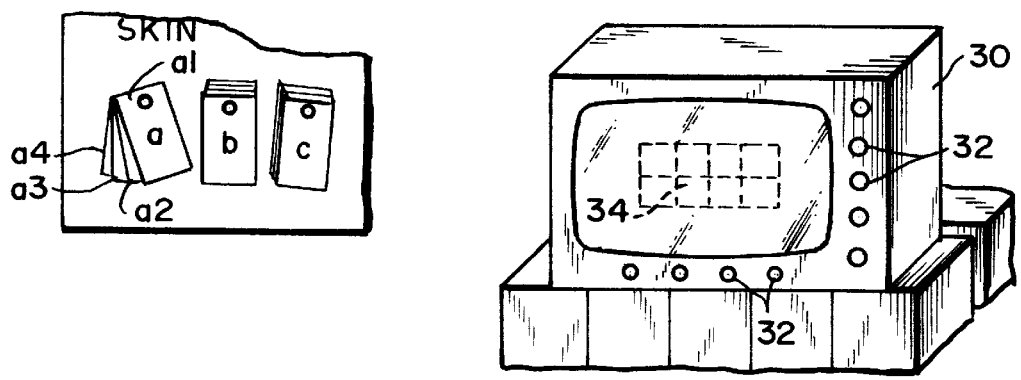
FIG.3
FIG.4
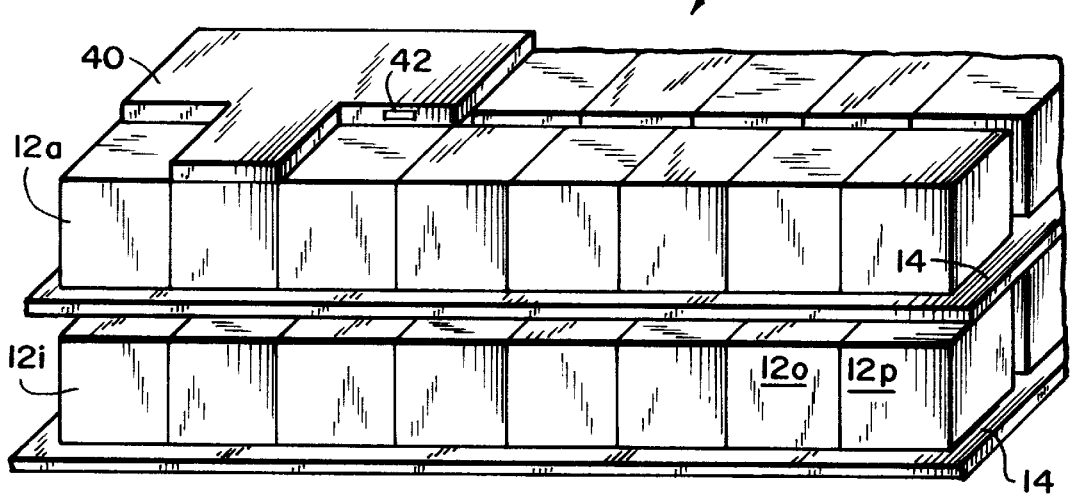

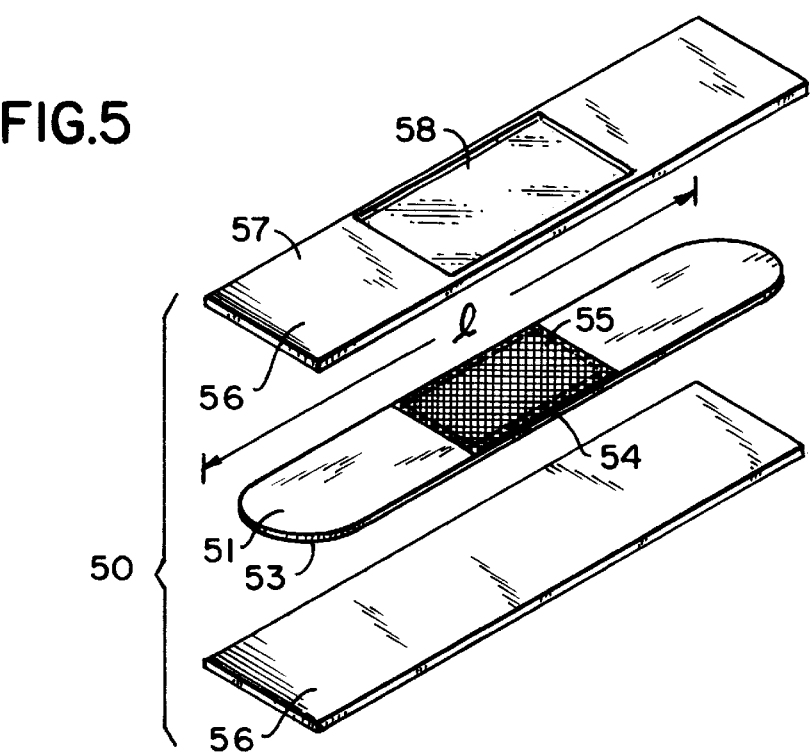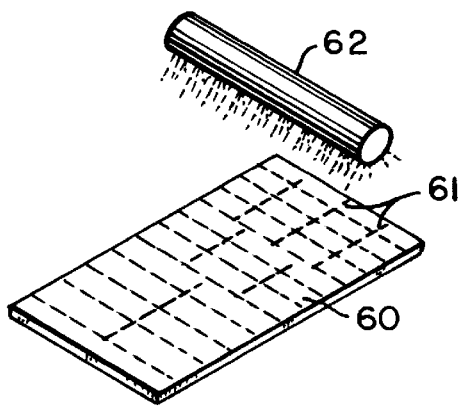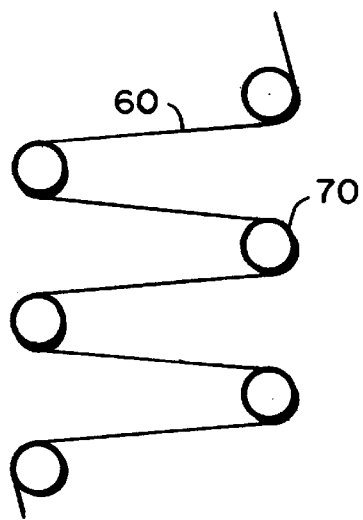

METHOD OF SELECTING AN ITEM TO MATCH A PERSON'S SKIN TONE

BACKGROUND OF THE INVENTION

The present invention is directed to a method of selecting an item which matches the skin tone of a person, and to a method of manufacturing an item to match a person's skin tone. More particularly, the present invention is directed to the selection of adhesive bandages in a matching skin tone, or the manufacture of adhesive bandages to match a particular skin tone.

The present invention applies especially to adhesive bandages of the type wherein an absorbent dressing is carried by an adhesive-coated backing; the type normally worn to cover superficial cuts, and often exposed to public view. However, the present invention also applies to adhesive bandages without the traditional gauze dressing, worn to conceal a scar or keloid. In fact, the invention applies to any product applied to the skin where it is desired that the product blend in with the wearers skin, so as to be, "invisible".

Adhesive bandages in skin tones matching that of the wearer have long been desired. However, it has grown to be expected that these adhesive bandages, even individual adhesive bandages, will be sterile wrapped. And this is the difficulty in offering the retail consumer a package of sterile bandages that match their individual skin tone. For years, wholesale production of adhesive bandages in enough colors to match any skin tone has proved impossible.

Stop gap measures provide matching skin tones for a few people. For example, adhesive bandages in a single pinkish-beige "flesh tone" have long been available in the United States, though the United States has consumers of many skin tones. Recently, a transparent plastic backing strip, revealing the skin tone of the wearer, has been used in an attempt to make an invisible bandage. However, the transparent strips leave the white of the gauze dressing exposed through the transparent backing. In addition, blood, or other wound secretions, may also be visible.

Various attempts have been made to hide the gauze in a transparent bandage, but have met with only mixed success. The desire for matching skin tone bandages remains unresolved. In fact, in the current market for children's bandages, the manufacturers have abandoned any attempt to match skin tone. A dozen different brands of children's adhesive bandages use many dozen brightly-colored cartoon like pictures, to decorate the bandage, or turn the bandage into a "tattoo".

U.S. Pat. No. 2,905,174 discloses an attempt to hide the gauze dressing of a transparent bandage by printing the backing with a "plurality of visible flesh colored markings". It is important to note that these markings are of the same color regardless of the skin tone of the customer. This structure presents a compromise. The markings over the gauze must be intense enough to help hide the gauze, but not so intense that the color of the wearers skin can't blend away the "flesh colored skin tones" of the markings. The patent suggests that the print pattern be made from opaque paints, in particular, rust brown and ocher from iron oxide, and carbon black; but the clear intent is to use the skin tone of the wearer to help blend-in the markings on the bandage. The skin tone of the wearer does not appear on the bandage.

U.S. Pat. No. 3,687.136 discloses a bandage with a transparent backing, a gauze dressing, and a piece of colored film therebetween to obscure the gauze dressing. The colors suggested are "white, black, yellow or bronze". Thus, a rectangle of one of these colors will be visible through the transparent backing.

U.S. Pat. No. 4,161,176 provides a bandage with many layers, releaseably secured atop one another, and the underlying bandage. Each layer is of a different color. This construction allows the wearer to peal off layers to select which color they desire. However, the layers have only a releasable fastening, and the color selected, as well as the remaining layers, may be easily stripped away. This sort of bandage construction also presents the user with many layers of easily accessible adhesive, which could make the bandage difficult to apply, and wear.

U.S. Pat. No. 5,586,971 discloses a bandage with an irregular edge, onto which a layer of makeup may be applied. It is intended that the make-up be "feathered in" about the edges, to blend-in with the skin tone of the wearer. The bandages of this patent, some without gauze pads, are perhaps more intended to hide the wound or scar than dress it. The "invisibility" of this bandage depends completely on the makeup, described at column 2, lines 41–43, as "any type of make-up including liquid, cream or stick types, provided they have the flowability and malleability to be able to be spread to effectively to cover the underlying adhesive tape". The examples given are of commercially available make up manufactured by e.g. Revlon, Inc. Make-up moves. The thicker the layer of make-up, the faster it moves. It moves laterally, smearing across the skin (or bandage), and it comes up, off the skin (or bandage).

U. S. Pat. No. 5, 120,325 discloses a bandage manufactured with a melanin or melanin-type pigment in, or on, the backing layer. An expanded description of these pigments, and how to achieve them, is presented at column 3, line 12 through column 4, line 30. A broad range of colors is included, but no description is given as to how to match a bandage to a skin tone, or how to select a matching skin tone bandage.

U.S. Pat. Des. 402,371 claims an adhesive bandage with an apertured brown plastic backing strip. There is no disclosure of a method of selecting a matching skin tone adhesive bandage, or a method of manufacturing such a bandage.

Store displays of paint or hair color often include a color chart or chips. Adjustment of a paint color is easy because it is a liquid. The blending of paints, on-site, to achieve a very close match to a particular color has been done for years. Matching hair color is often not the purpose of the purchase. The new color supplants the old, wherever it is applied. Matching is not required. The contrast of the new hair color is, hopefully, "coordinated" with the existing skin tone.

The method of manufacture, and/or selecting, a matching skin tone bandage according to the present invention is not disclosed or suggested by any of the above.

SUMMARY OF THE INVENTION

In one embodiment of the present invention, a method of selecting an item to match a skin tone, a person, compares their skin tone to the plurality of skin tones in which the item is provided. The retail display of the item. may include an array of this plurality of colors, from which the person compares and selects the matching skin tone. The display may have multi-level arrays, to provide a closer match. The matching color may be given a particular name or other indicia, and the corresponding name or indicia provided on the package with bandages of that particular skin tone. Thus the purchaser to may select matching skin tone bandages.

Alternatively, a scanner may be provided, for comparing and selecting the matching skin tone, or indicia.

According to another embodiment of the present invention, means are provided to develop the selected skin tone on an item, such as an adhesive bandage. The bandages are manufactured as is customary in sterile, individual wrappers. In this embodiment, the backing layer comprises skin tone developing ingredients, in a skin tone developing region. These ingredients may be "developed" to the matching skin tone while still in the sterile wrapper. When using light to develop the ingredients, the wrapper may have a transparent window adjacent the skin tone developing region. A scanner may be provided to compare and select a matching skin tone color, or duplicate the skin tone scannned.

In addition, it is within the scope of the present invention to scan and print, or develop, gauze "blocks" in a skin tone matching a person's skin tone. The block may be provided with a pressure sensitive adhesive layer to firmly secure it to the transparent backing layer of a bandage. In this manner, an individually sterile wrapped bandage having a transparent backing may be first applied to a person's skin, and then rendered invisible by placing the gauze block over the backing strip, concealing the dressing or wound. The block may be provided in a number of sizes, to cover all or part of the backing. When a skin friendly adhesive layer is used, the gauze block will have utility as a dressing-less, or cosmetic, bandage.

The method of manufacture or selection of the present invention may be used to select many items, such as a single adhesive bandage, a wrap-around "ace bandage", a sweatband, or, e.g. "talc" body powder. According to the present invention, the selection, and/or manufacture of the item in the matching skin tone may be made on site at a retail facility, a hospital, or a doctor's office.

BRIEF DESCRIPTION OF THE DRAWINGS

FIG. 1 is a partial, top perspective view of a retail display of bandage packages, packaged in a pre-selected plurality of colors, with an array of the plurality of colors.

FIG. 2 is a partial, cut-away view of a multi-level array for a display, such as that shown in FIG. 1.

FIG. 3 is a top perspective view of another store display, utilizing a video monitor to compare and select the skin tones.

FIG. 4 is a perspective view of a scanner for viewing and selecting a person's skin tone.

FIG. 5 is an exploded perspective view, of an individually wrapped, sterile bandage.

FIG. 6 is schematic of a method of manufacture according to the present invention, illustrating a light source, for developing the matching skin tone of the bandages before dispensing the bandages.

FIG. 7 is a schematic side view of a plurality of heating rollers through which the bandage sheet may be wound, to develop the matching skin tone.

DETAILED DESCRIPTION OF THE INVENTION

Figure 8:
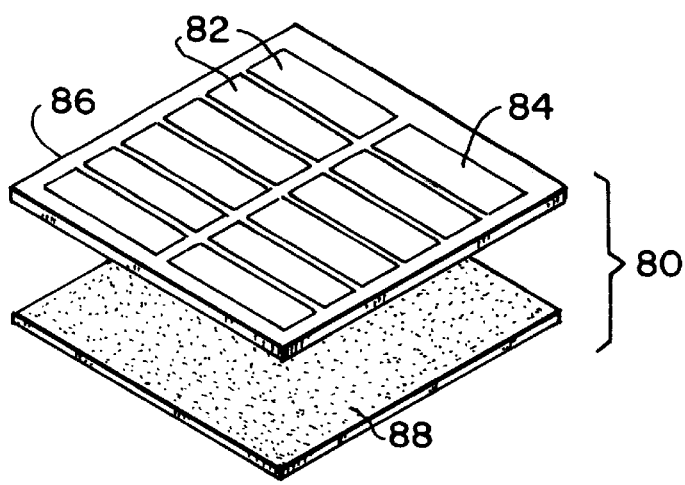
FIG. 8 is an exploded perspective view, of a sheet of preformed gauze blocks.

One embodiment of the present invention, a method of selecting an item to match a person's skin tone, is described in relation to FIGS. 1–10. In FIG. 1, a retail display of the items, shown generally at 10, comprises packages, 12a–12h, of the product, e.g. bandages, manufactured in a pre-selected plurality of skin tones, a–h, and set out on shelf 14. The pre-selected plurality of colors are chosen to most closely approximate, or blend in with, the anticipated skin tones of the expected purchaser. The display, 10, of bandage packages, 12a–12h is provided with a chart, illustrating the array, 16, of the plurality of pre-selected skin tones. The purchaser matches their skin tone to the array of skin tones, provided in the display. The display may have multi-level arrays, to provide the match. FIG. 2, illustrates an example of a multi-level array which permits the purchaser to select a bandage with matching skin tone. As shown in FIG. 2, the first skin tone selection, e.g. "a" may yield a stack of color cards a1-an, in this illustration a4, of related hues.

The purchaser makes the selection as follows: using the array (or arrays) the purchaser compares their skin tone (or a desired skin tone) to the pre-selected skin tone colors of the array(s), and selects the matching color in the array(s). The matching color may be given a particular name or other indicia, and the color, its corresponding name, or indicia provided on the package with bandages of that particular skin tone. Thus the purchaser to may select a matching skin tone bandage.

The total number of colors pre-selected may preclude sufficient packages being available at the display. Thus, selection of the product may occur at the display, but the package picked up later, or picked up at the check-out counter or service counter. Alternatively, the product may be shipped to the purchaser.

If the packages are not present in the display, but must be picked up at another location, such as the check-out or service counter, additional means may be provided to correctly communicate the matching color to the pick up location. These means could comprise anything from an electronic transmission to the pick up location, to the purchaser's selecting e.g. a paper tab or receipt, provided at the display, indicating the matching color and/or indicia.

Alternatively, the array may be presented on a video monitor, 30, in FIG. 3. The selection of the matching skin tone may be made with the knobs or buttons, 32, or by touching the screen, 34, as is well known. [Similar means are customary in automated teller bank machines.] An electronic image of the first level of the array offered by the chart in FIG. 1, may be the default display in the store. When using a video monitor, one can have many colors in sub-arrays, represented by sequential screen images. For example, a first selection from the first level, or default array, on the screen might lead to a second level array, generated by the first choice, from which a closer match could be made. Similarly, a third level sub-array might also be available from which to select an even closer match.

If desired, a scanner shown at 40 in FIG. 4, may be used to compare and select among a great number of skin tones. This will provide a purchaser with a convenience, and perhaps a better match. Not all people can make color matches, and fewer can make sophisticated color matches, especially knowing when to match up or down in relation to a hue. The scanner may be easily programmed to make the selection from among the plurality of skin tones. Once the selection is made, the matching skin tone, or its indicia, is displayed in window, 42.

The above description of the method of selection of the present invention has been described in relation to a particular product, namely pre-made, sterile, individually wrapped, multi-pack bandages. The method of the present invention may also include a method of manufacturing such bandages in a matching skin tone.

It is specifically within the scope of the present invention to match the skin tone of the person, by providing the "manufacturing" elements, which print or develop the precise skin tone, at e.g., the store or doctor's office. Thus, a person could select a skin tone from a pre-selected array of skin tones, or a scanner view and record the person's skin tone, and bandages would be produced right there, to that selected skin tone.

To produce the matching skin tone in a sterile, wrapped adhesive bandage requires the wrapped bandages contain skin tone developing ingredients to be activated by, e.g. heat or light. It is preferred that these ingredients be present in or on the backing layer, to keep them remote from the dressing. To facilitate manufacture, it is within the scope of the invention to provide backing ingredients on a separate layer, such as a plastic layer, to be secured to the backing.

The developing ingredients will be determined by the technique chosen to create the skin tones on the wrapped bandages. Thermal printing onto impregnated sheets, as was used to copy architectural drawings may be used. Alternatively, Polaroid-type instant developing technology can be used, but this requires a fairly transparent window in the wrapper.

Preferably, a scanner could be provided, and the matching bandages in the selected sin tone produced on site. Depending on the color developing capability of the backing layer, the scanned skin tone could be used to manufacture a duplicate skin tone.

FIG. 5 illustrates a sterile, wrapped adhesive bandage 50 formed for this embodiment of the invention. The bandage has a backing layer, 51, with a pressure sensitive adhesive surface, 53, and a dressing, 54, secured to the adhesive surface, 53. Sterile bandages maybe supplied to a retail establishment, together with the means to scan the skin tone desired, and develop the desired skin tone in the entire backing layer of a wrapped bandage. If desired, the backing layer may be transparent, and the ingredients to develop the desired skin tone located in just the region, 53, above the dressing. If desired, the region, 55, may extend the entire length, 1, of the backing layer. The bandage is contained within a sterile wrapper formed of sheets, 56, joined together about the perimeter of the bandage. When light will be used to develop the skin tones, the sheet, 57, adjacent the backing layer has a transparent window, 58. This window will also reveal the skin tone of the wrapped bandage. The sheets may be formed of paper, plastic, fabric, or laminates thereof. The only requirement for the sheet material being that it maintains sterility in the unopened wrapper. The choice of ingredients to develop the color in the wrapped bandages should be such as will not effect the sterility or safety of the products. Though the skin tone may be scanned, e.g. at a store, and the sterile matching bandages manufactured off-site and shipped to the store or customer, the time delay is probably not desired.

Sterile consumer bandage products are sold in a multi-bandage package, either in a sheet of bandages, which may be folded to fit inside the package, or separated into individual bandage wrappers. FIG. 6 illustrates a sheet, 60, of pre-manufactured bandages, 50. The sheets are provided with lines, 61, of perforations or weakening of the sheet material to facilitate folding and/or tearing of the sheet. The bandages may be separated from each other along the lines 55, either before packaging, or by the user.

It is believed that developing the matching skin tone within a sterile package of bandages is best accomplished with radiant energy, in the form of heat, or light. FIG. 6 illustrates the application of radiant energy from a source 62, to the skin tone developing region, 55, of the backing layer 51. Maintaining the bandages in a sheet permits the developing of the matching skin tone in the bandages of the entire sheet. The skin tone developed in the bandage backing by the source, 62 will be determined by a number of variables, including the intensity of the source and time of exposure, but the methods are well known in color printing and/or photography. When manufacturing a bandage of matching skin tone by developing the color in the wrapper, it is preferred that sheet, 57, be transparent.

FIG. 7 illustrates another method of providing radiant energy to the bandages, through the means of heated rollers, 70. Development of the precise colors may be achieved, e.g. by passing the bandage or sheet of bandages about a different number of rollers, thereby increasing the amount of energy applied thereto. Alternatively, the rollers may be set to operate at different speeds or temperatures. Similar adjustments are known to one skilled in the art. It should be noted that dressing blocks, sterile wrapped or not, may also be developed to the matching skin tone using the same backing materials as described in the manufacture of the bandages.

In another embodiment of the present invention, bandages with a transparent backing may be sterilized and wrapped, and sold with a gauze block of matching skin tone. The gauze blocks, intended to be placed over the backing so as to conceal the dressing or wound, need not be sterile wrapped. The gauze block should be constructed of a material of comparable to or which does not appreciably affect the beneficial characteristics of the backing layer. It is required that the gauze block match the desired skin tone on one surface thereof, and that the opposite surface have a layer of permanent adhesive, or other similar means, to attach the piece to the backing. The skin tone matching block is attached over the dressing, to conceal the dressing. The block is referred to as a gauze block to indicate its position, but it is understood that the bandage dressings are not limited to gauze, and may be formed of a variety of materials.

FIG. 8 illustrates a sheet, 80, of gauze blocks, 82, comprising a layer of backing material, 84, having a layer of permanent adhesive on one surface, 86, and a layer of release material, 88, covering the adhesive. Sheet, 80, may be color printed to the desired color, and scored to permit the consumer to more easily separate the blocks. Alternatively, the gauze blocks may be separated prior to final packaging of the gauze blocks. The gauze blocks may be packaged and sold with, or separately from, the transparent bandages.

Figure 9:
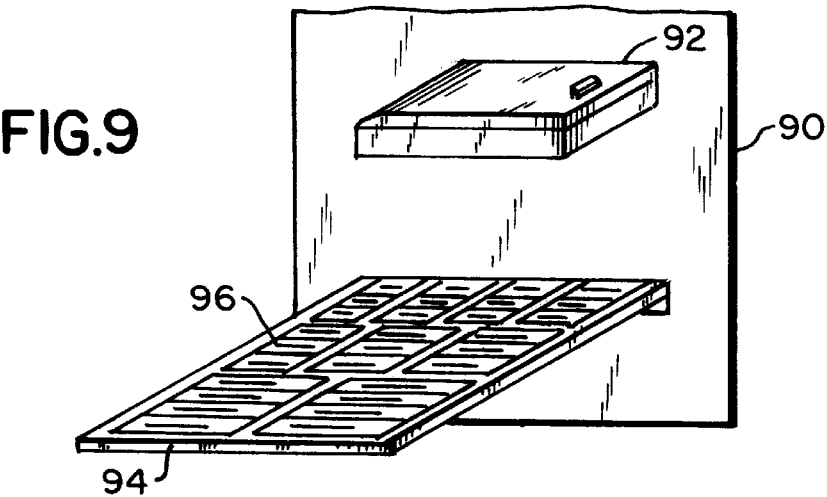
FIG. 9 is a schematic of a means for manufacturing gauze blocks, according to the present invention.
Figure 10:
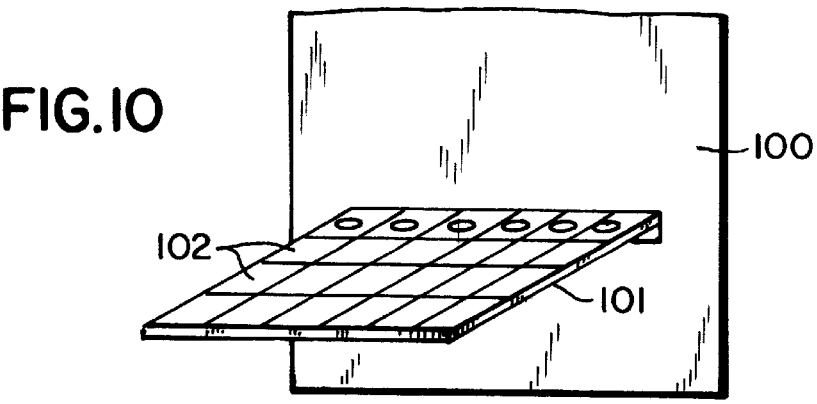
FIG. 10 is a schematic of another means for manufacturing gauze blocks, according to the present invention.

As seen in FIG. 9, the block manufacturing retail dispenser, 90, may include a scanner, 92, to scan, compare and select the skin tone. Printing means of a conventional sort are provided in dispenser, 90, to print the non-adhesive surface of the blocks with the matching skin tone. The printed blocks, 94, are dispensed in a sheet, 96, as shown, or may be pre-folded, and/or separated from each other, and placed in a package before dispensing. The blocks may be sized to extend the entire length of conventional bandage backing strip, or just the extent of the dressing. FIG. 10 illustrates a sheet, 101, of skin tone matching blocks, 102, of dressing size, in a variety or bandage sizes and shapes, being ejected from retail dispenser, 100.

The present invention is not to be considered limited in scope by the specific embodiments described above, since the described embodiments are intended only to be illustrative of particular aspects of the invention. Modifications of the above-described embodiments and modes for carrying out the invention that are obvious to those skilled in the medical and cosmetic arts are intended to be within the scope of the following claims.

What is claimed is:

1. An adhesive bandage, comprising a flexible backing, a pressure-sensitive adhesive on one side of said backing, and an absorbent pad, carried by said backing on said one side, said backing having a skin tone developing region comprising skin tone developing ingredients which are activated by heat or light to produce the desired skin tone, said region extending at least across the portion of the backing where the pad is carried.

2. The adhesive bandage of 1, further comprising a wrapper surrounding said bandage which preserves the sterility of said bandage, and wherein said wrapper comprises a transparent window above the skin tone region.

3. The adhesive bandage of 1, wherein the backing is transparent, and the adhesive is transparent.

4. In an adhesive bandage having a flexible backing, a pressure-sensitive adhesive on one side of said backing, an absorbent pad carried by said backing on said one side; the improvement comprising said backing having a skin tone developing region comprising skin tone developing ingredients which are activated by heat or light to produce the desired skin tone.

5. A method of manufacturing a sterile adhesive bandage in a color that matches the color of a person's skin, said method comprising the steps of:

1) comparing the skin tone of a person with one or more of a plurality of colors to determine the closest match; and subsequently 2) selecting the color which most closely matches that person's skin tone; and subsequently 3) manufacturing a sterile adhesive bandage having a backing layer with that person's selected color.

6. A method of manufacturing a sterile adhesive bandage in a color that matches the color of a person's skin, said method comprising the steps of:

(1) automatically scanning the skin of a person and storing the skin tone color; and (2) manufacturing an item with the stored color.

7. A method for manufacturing matching skin tone bandages comprising the steps of:

manufacturing a bandage comprising a film strip backing, a dressing, and an adhesive layer extending along one surface of the backing layer and securing the dressing to the backing layer, the backing layer comprising skin tone developing ingredients, packaging and sterilizing the individual bandages, determining a desired skin tone, and irradiating the sterile bandages to develop the desired skin tone in the bandage.

8. The method of claim 5, further comprising the step of packaging the individual bandages to maintain their sterility.

* * * * *